United States Patent
Montross et al.

(10) Patent No.: US 11,273,045 B2
(45) Date of Patent: Mar. 15, 2022

(54) MOTION TOE SYSTEMS AND METHODS

(71) Applicants: William Montross, Colorado Springs, CO (US); Lee Strnad, Richfield, OH (US)

(72) Inventors: William Montross, Colorado Springs, CO (US); Lee Strnad, Richfield, OH (US)

(*) Notice: Subject to any disclaimer, the term of this patent is extended or adjusted under 35 U.S.C. 154(b) by 11 days.

(21) Appl. No.: 17/005,957

(22) Filed: Aug. 28, 2020

(65) Prior Publication Data

US 2021/0059829 A1 Mar. 4, 2021

Related U.S. Application Data

(60) Provisional application No. 62/893,068, filed on Aug. 28, 2019.

(51) Int. Cl.
*A61F 2/42* (2006.01)
*A61F 2/30* (2006.01)
*A61F 2/46* (2006.01)

(52) U.S. Cl.
CPC ........ *A61F 2/4225* (2013.01); *A61F 2/30767* (2013.01); *A61F 2/4606* (2013.01); *A61F 2002/4233* (2013.01)

(58) Field of Classification Search
CPC .............. A61F 2/4606; A61F 2/4225; A61F 2002/4233
See application file for complete search history.

(56) References Cited

U.S. PATENT DOCUMENTS

| | | | | |
|---|---|---|---|---|
| 5,037,440 A | * | 8/1991 | Koenig | A61B 17/1682 623/21.19 |
| 2008/0221697 A1 | * | 9/2008 | Graser | A61F 2/4225 623/21.19 |
| 2012/0259312 A1 | * | 10/2012 | Iannotti | A61B 17/88 604/506 |
| 2012/0259419 A1 | * | 10/2012 | Brown | A61F 2/4225 623/21.19 |
| 2018/0036142 A1 | * | 2/2018 | Wahl | A61B 17/1775 |

FOREIGN PATENT DOCUMENTS

FR 3022137 A1 * 12/2015 ............. A61B 17/15

* cited by examiner

*Primary Examiner* — Javier G Blanco
(74) *Attorney, Agent, or Firm* — BrainSpark Associates, LLC

(57) ABSTRACT

Disclosed are devices and related surgical methods for replacing some or all of a metatarsophalangeal joint of a patient.

3 Claims, 22 Drawing Sheets

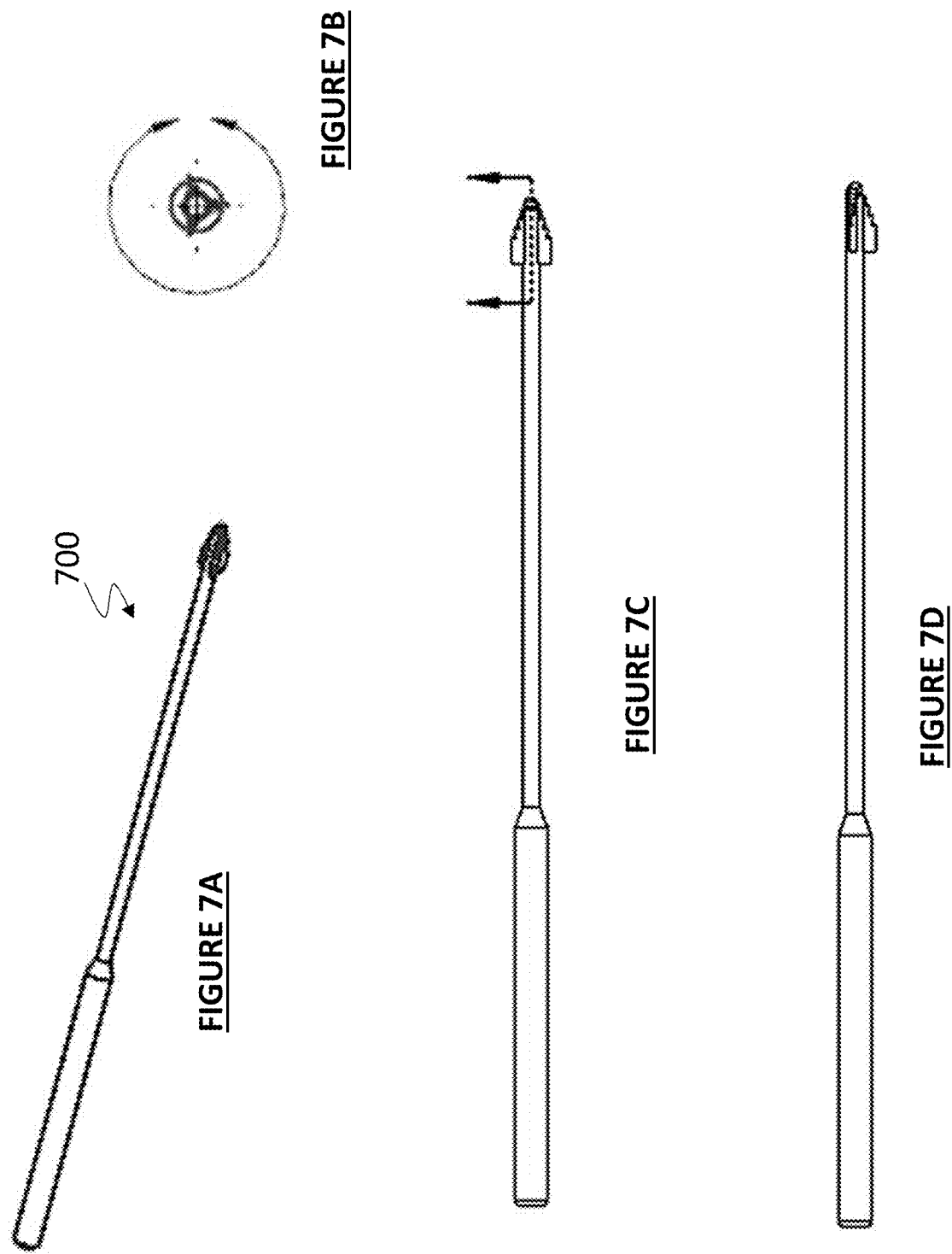

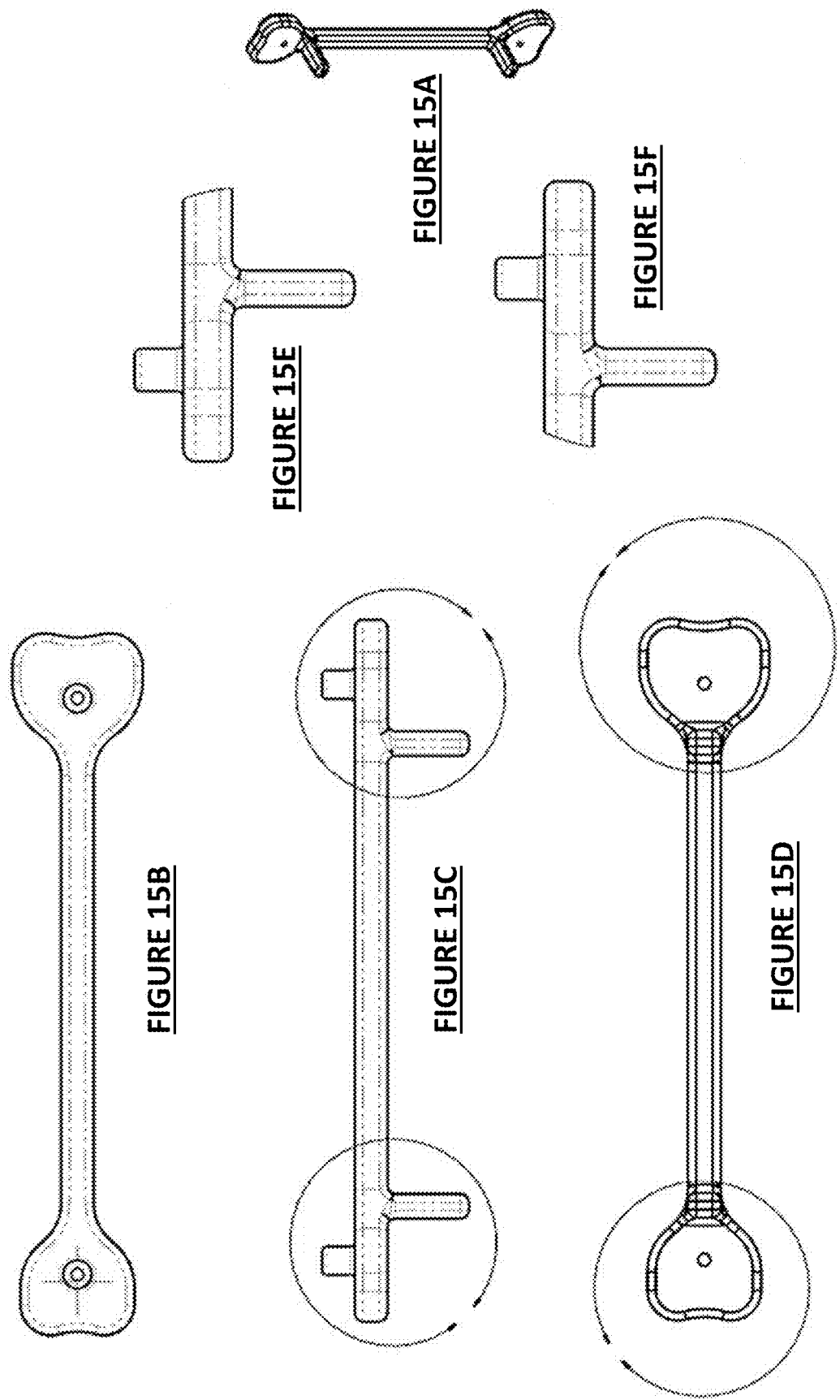

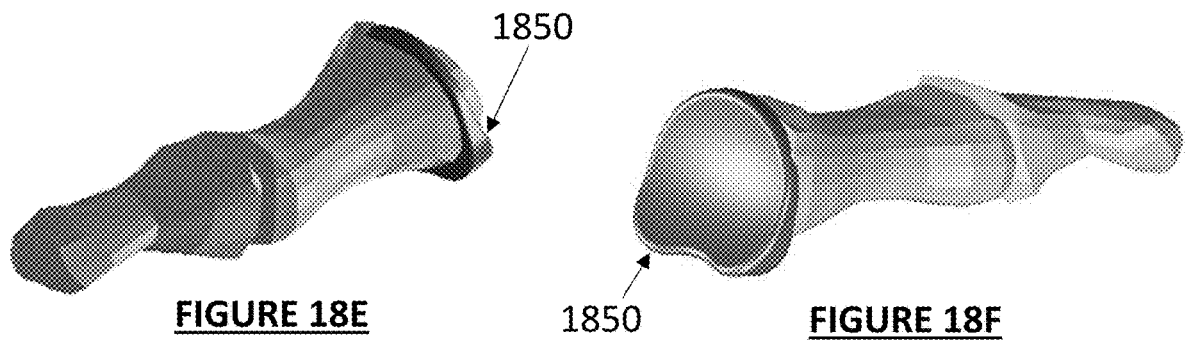
FIGURE 18E     1850     FIGURE 18F
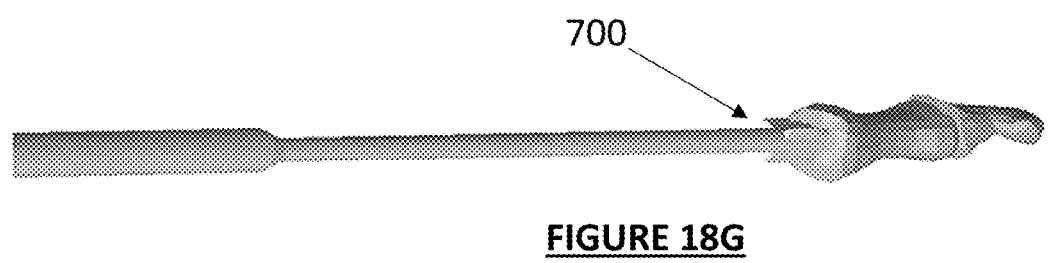
FIGURE 18G
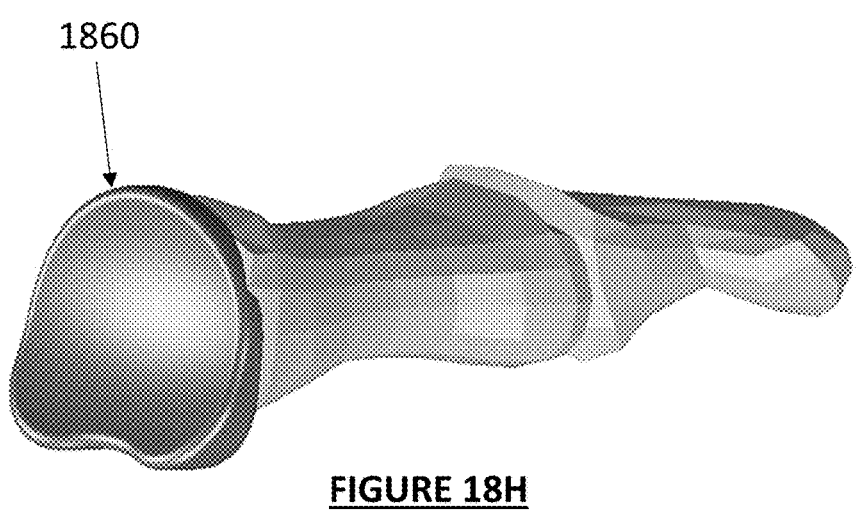
FIGURE 18H

MOTION TOE SYSTEMS AND METHODS

CROSS-REFERENCE TO RELATED APPLICATIONS

This application claims the benefit of U.S. Provisional Patent Application Ser. No. 62/893,068 entitled "MOTION TOE SYSTEM," filed Aug. 28, 2019, the disclosure of which is incorporated by reference herein in its entirety.

TECHNICAL FIELD

The present invention relates generally to devices and methods for surgically repairing and/or replacing diseased or degenerated natural joints, such as the metatarsophalangeal joint.

BACKGROUND

*Hallux rigidus* is a degenerative condition of the first metatarsophalangeal (MTP) joint of the great toe. It is characterized by progressive loss of motion, particularly dorsiflexion. This, along with osteophyte formation, can result in pain and stiffness. The condition tends to affect patients in the fourth and fifth decades and, when severe, can result in significant disability.

To establish a diagnosis of *hallux rigidus*, plain radiographs are the investigation of choice, along with clinical examination. Radiological appearances are varied: dorsal osteophytes are primarily the sole finding in early stage disease, with progression to significant joint space narrowing, periarticular cystic changes and involvement of sesamoids as the disease progresses. A classification system described by Coughlin and Shurnas in 2003 uses a combination of clinical and radiological findings and is a commonly used tool for grading the severity of disease.

In addition to the stage of disease, the extent of any associated deformity, and patients' age and activity level are also considered when deciding on surgical treatment. Traditionally, mild to moderate disease has been treated with cheilectomy or osteotomy, with more severe cases being treated with arthrodesis. More recently, treatment using joint replacement, either by means of hemiarthroplasty or total arthroplasty of the MTP joint, is becoming an increasingly popular option for patients with advanced disease.

Total first metatarsophalangeal arthroplasty is a surgical procedure for treatment of moderate-to-severe *hallux rigidus* in patients for whom arthrodesis of the first MTP joint may not provide adequate satisfaction due to the inherent stiffness of the *hallux*. This surgical procedure can be performed by a single surgeon using a standardized approach technique, with the patient supine and under general anesthesia. A mid-thigh pneumatic tourniquet may be used. The first MTP joint can be approached through a dorsomedial skin incision. A longitudinal capsulotomy can be performed in line with the skin incision. AH osteophytes can be removed from the distal metatarsal and proximal phalanx, if necessary, followed by sesamoid mobilization from the plantar aspect of the joint.

The goal of *hallux rigidus* surgery is relief of pain and restoration of function by preserving joint mobility. Total joint replacement arthroplasties are desirably developed to overcome the disadvantages presented by arthrodesis, which is still considered the treatment of choice for advanced-stage *hallux rigidus*. However, loss of joint motion may not be acceptable for active patients who aim to resume recreational and sports activities. Furthermore, a functional great toe is important considering its role during gait. In healthy subjects, the forces during the push-off phase under the first metatarsal head and *hallux*, taken together; can account for about 53% of the body weight.

SUMMARY OF THE INVENTION

In various aspects, embodiments of the invention include recognition of a need in the art for improved tools, techniques, implant components and/or surgical procedures for the surgical repair and/or replacement of diseased or degenerated natural joints, such as the metatarsophalangeal joint.

In various embodiments, a surgical system is described which designed to replace the head of the first metatarsal, the base of the proximal or both at the same time. This system desirably aids the surgeon to make decisions at the most crucial time: i.e., during the surgical procedure. Unlike previously existing systems and techniques, a surgeon using the disclosed systems and methods is able to replace the joint based upon visual inspection and not a two-dimensional x-ray. No longer will the surgeon find upon opening the first metatarsal phalangeal joint that the side of the joint he wanted to replace is the normal side.

In various embodiments, one a joint is cleaned of peripheral spurs and/or other structure, the guides can optimally sit accurately on the bone in the dorsal plantar position, desirably giving the implant the best fit possible and avoid putting an implant that is too large in one or more dimensions, which can cause jamming and/or further limit motion. Once the guide is set dorsal and plantar, this will desirably "free up" the surgeon to aim the guide down the shaft of the metatarsal and phalanx. This is a significant improvement compared to some existing systems, in which the surgeon is unable to maintain the horizontal position or the vertical position simultaneously. To comply with normal hospital policies regarding sterilization, the various components of this system can be provided as pre-sterilized and/or disposable—which eliminates the need for "dropping off" a set several days in advance for sterilization in advance of the surgical procedure.

BRIEF DESCRIPTION OF THE DRAWINGS

The foregoing and other objects, aspects, features, and advantages of embodiments will become more apparent and may be better understood by referring to the following detailed description of the preferred embodiments, taken in conjunction with the accompanying drawings, wherein:

FIGS. 7A through 7D depict various views of a fin cutting instrument;

FIGS. 15A through 15F and 16A through 16F depict exemplary embodiments of phalanx guides;

FIGS. 18A through 18H depict exemplary steps for preparing a phalanx bone and implanting a phalanx implant component.

DETAILED DESCRIPTION

Figure 1:
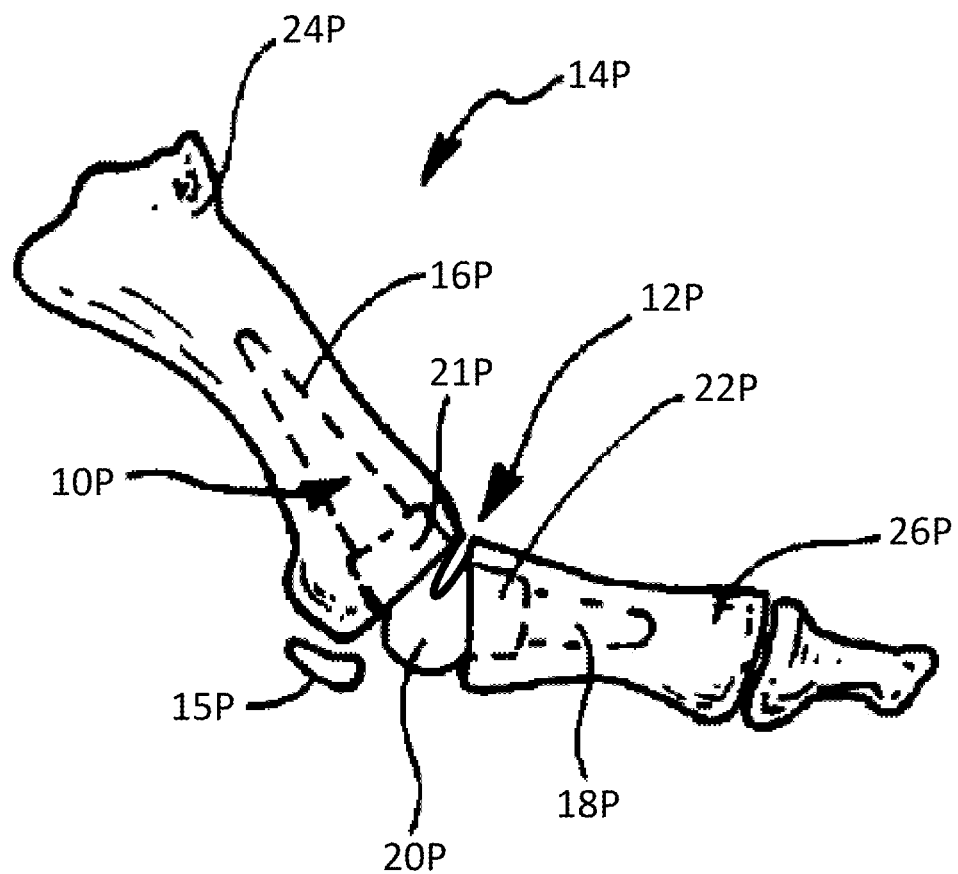
FIG. 1 is a side plan view of a prior art toe implant positioned in a flexed great toe.
Figure 2A:
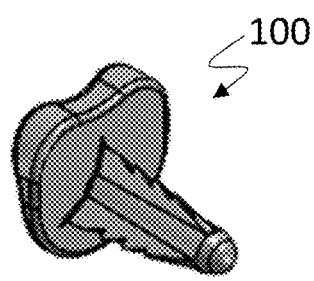
FIGS. 2A through 2G depict various views of one exemplary embodiment of a phalanx base implant component.
Figure 2B:
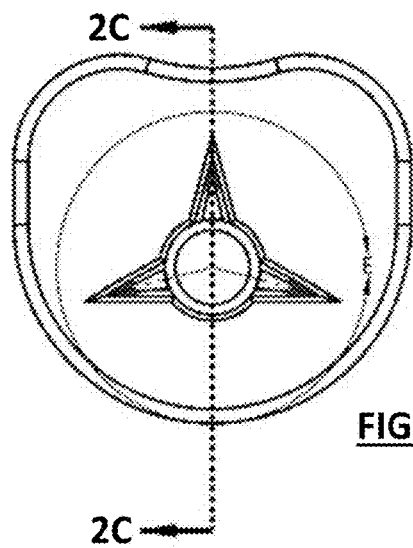
Figure 2C:
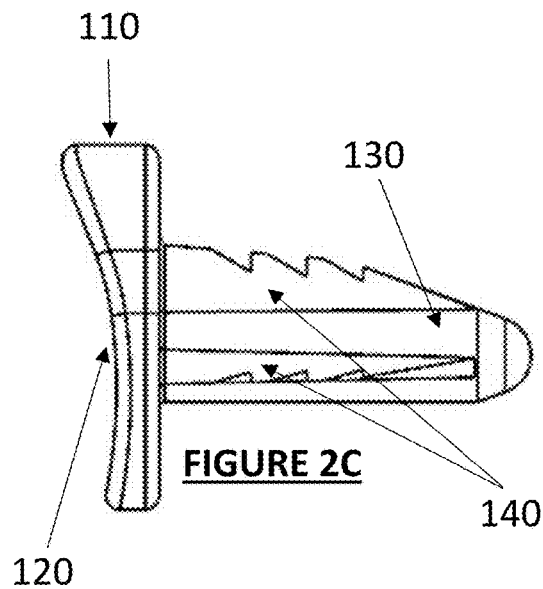
Figure 2D:
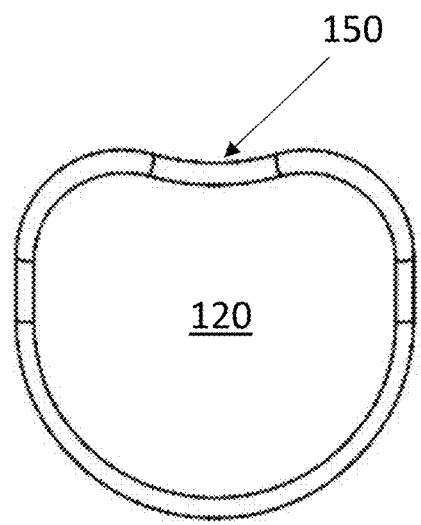
Figure 2E:
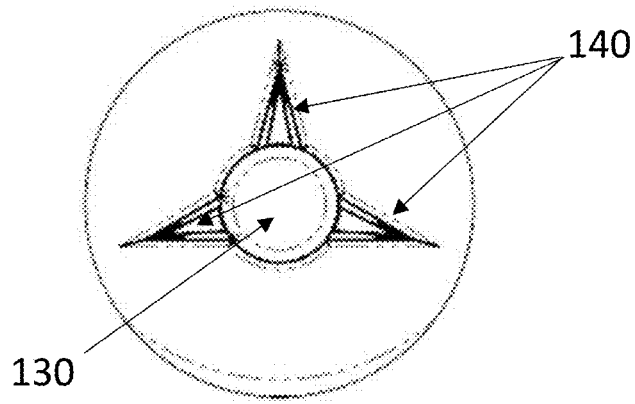
Figure 2F:
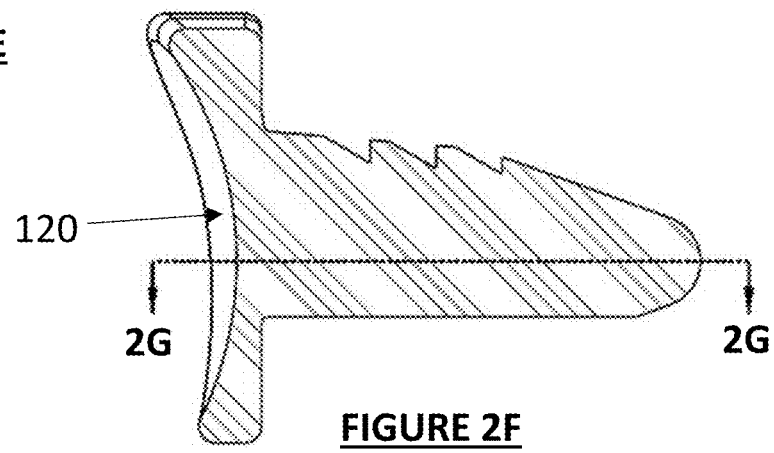
Figure 2G:
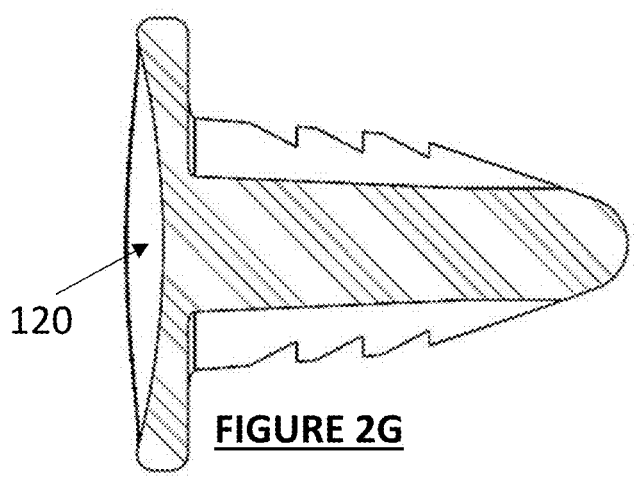
Figure 3A:
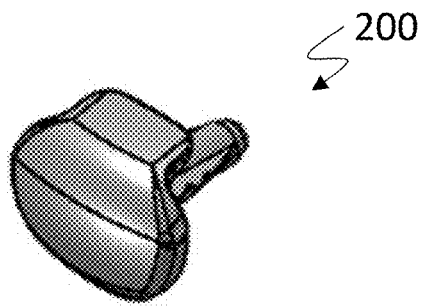
FIGS. 3A through 3H depict various views of an exemplary embodiment of a metatarsal head implant component.
Figure 3B:
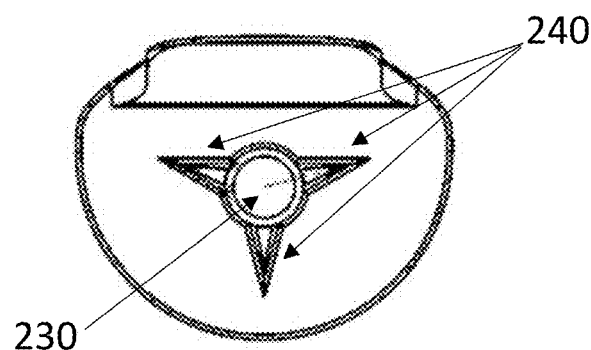
Figure 3C:
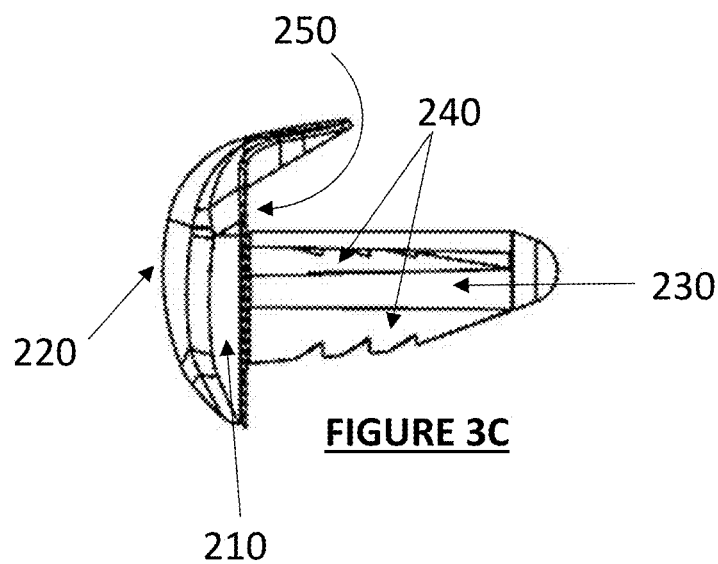
Figure 3D:
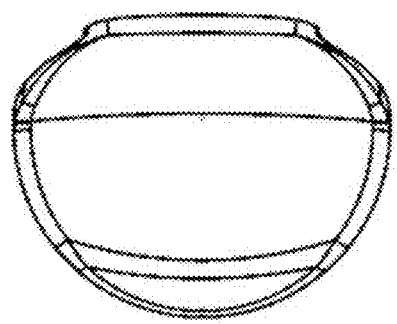
Figure 3E:
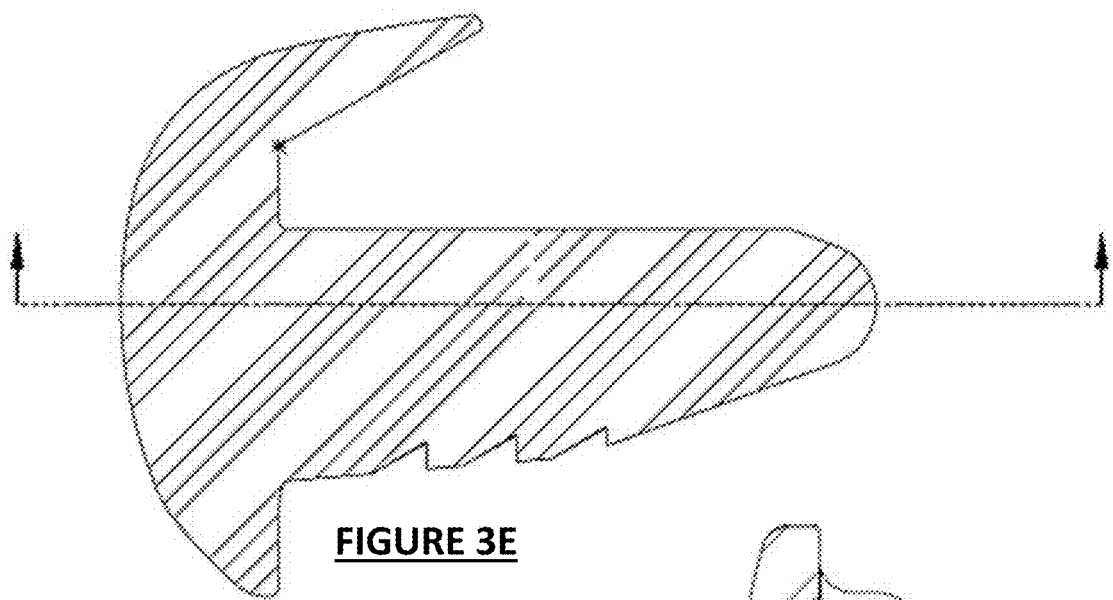
Figure 3F:
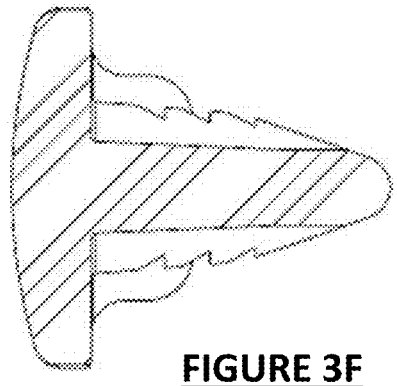
Figure 3G:
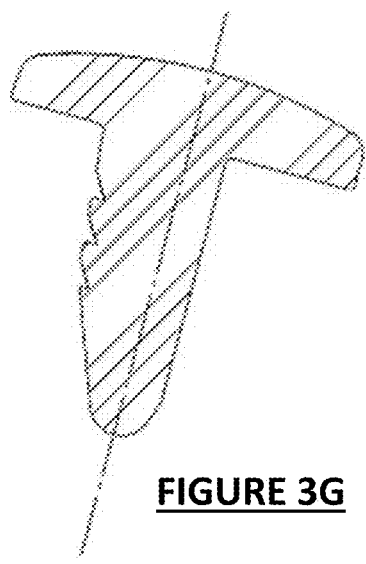
Figure 3H:
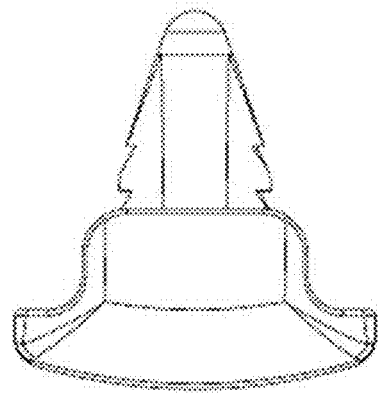

Various features of the present invention include the recognition of a need for a more effective and versatile system for the surgical repair and/or replacement of diseased or degenerated natural joints, such as the metatarsophalangeal joint. In various medical applications, the disclosed components and related surgical tools and techniques can desirably facilitate the treatment of a variety of sizes and/or shapes of patient anatomy, which can be important to achieve the most accurate and best performance and/or fit of implant components and well as facilitate patient recovery.

This specification describes novel systems, devices and methods to treat degenerated natural joints, such as the metatarsophalangeal joint. It should be appreciated, however, that various aspects of the present invention may not limited in their application to only the metatarsophalangeal joint. The systems and methods may be applicable to the treatment of fractures or other degeneration of other diverse bone types. Embodiments will now be described with reference to the drawings, wherein like reference numerals are used to refer to like elements throughout. It should be understood that the figures are not necessarily to scale.

FIG. 1 depicts a prior art implant 10P (partly in phantom) positioned in a first metatarsal phalangeal joint 12P of a great toe 14P, with the toe 14P being flexed. Additionally, the sesamoid apparatus 15P is illustrated. The implant 10P includes a proximal stem 16P, a distal stem 18P, a hinge 20P and a pair of metal grommets 21P and 22P. The proximal stem 16P is inserted into the metatarsal 24P while the distal stem 18P is inserted into the proximal phalanx 26P. The implant 10P is designed to flex at the center of the hinge 20P. The grommets 21P and 22P are positioned on opposite sides to the hinge 20P. The implant 10P is sold by Wright Medical Technology, Inc. located in Arlington, Tenn., under the trademark SWANSON®. Unfortunately, the results obtained with the implant 10P illustrated in FIG. 1 are not entirely satisfactory. More specifically, the implant 10P must deform to accommodate the anatomy of the first metatarsal phalangeal joint 12P. As a result thereof, the implant 10P tends to drastically limit the range of motion of the joint 12P, often increasing the stress at the joint 12P and/or altering the normal flexing of the toe 14P. Furthermore, the deformation of the implant 10P can cause binding in the joint 12P. In addition, the grommets 21P and 22P can potentially contact during flexing of the toe 14P. Furthermore, the cuts to metatarsal 24P and/or the proximal phalanx 26P required to make space for the implant 10P can significantly interfere with the sesamoid apparatus 15P or the flexor hallucis *brevis* attachment (not illustrated in FIG. 1), which can significantly influence how the toe 14P functions with the implant 10P.

In light of the above, it is an object of the present invention to provide a toe implant for the first metatarsal phalangeal joint for the great toe that provides increased available range of motion. Another object of the present invention is to provide a toe implant that allows the toe to move in a fashion that better simulates the natural motion of the first metatarsal phalangeal joint. Still another object of the present invention is to provide a toe implant that does not significantly increase the stresses at the joint or alter the normal flexing of the toe. Yet another object of the present invention is to provide a toe implant that does not interfere with the sesamoid apparatus or the flexor hallucis brevis attachment. Another object is to provide a toe implant that provides relatively good joint mobility, relatively good load transfer, relatively good toe stability, and relatively good toe purchase. Still another object is to provide a toe implant that is relatively easy to insert into the first metatarsal phalangeal joint.

FIGS. 2A through 2G depict various views of one exemplary embodiment of a phalanx base implant component 100 for implantation into a proximal phalanges of the big toe, and FIGS. 3A through 3H depict various views of an exemplary embodiment of a metatarsal head implant component 200 for implantation into a distal portion of the metatarsal bone, which can be utilized individually to utilized to replace the base of the proximal phalanges, the head of the first metatarsal or both at the same time (i.e., a total joint replacement of the Metatarsophalangeal joint of the big toe).

As best seen in FIGS. 2A through 2G, the base implant 100 includes a head 110 having an articulation surface 120 and a base stem 130. The articulation surface 120 is desirably designed to replicate the articulating surface area of the natural base of the proximal phalanx, with the base stem 130 designed to fit anatomically into an intramedullary canal of the phalanx bone (i.e., the natural shaft location). One or more fins 140 (in this embodiment, three fins) are positioned on the shaft, and these fins desirably provide secure anchoring and fixation of the base implant 100 to the bone. The fins are also desirably configured to allow stability and prevent rotation of the base implant 100 once implanted into the bone. The base implant 100 also includes a bottom groove 150, which can be designed to follow a natural shape of the base of the proximal phalanx (not shown), which includes a grooved structure to allow the flexor tendon (not shown) to pass through, and desirably avoid becoming irritated (which can commonly occur with non-grooved implants). Desirably, the head 100 of the implant 100 is relative thin in depth and/or thickness, wherein this relatively thin head design effectively provides "resurfacing" of the base of the proximal phalanx without unduly expanding and/or "stretching" the overall size and/or thickness of the Metatarsophalangeal joint, which desirably maintains the natural articulation and structural relationship between the bones and/or connective tissues of the joint for improved longevity and function of the joint replacement.

As best seen in FIGS. 3A through 3H, the head implant 200 includes a head 210 having an articulation surface 220 and a head stem 230 with one or more fins 240, wherein the stem desirably fits down the natural intramedullary shaft of the distal portion of the first metatarsal, with the fins 240 engaging surrounding bone to provide for adequate fixation and/or rotational/torsional stability. In various embodiments, the shape of the articulation surface is desirably selected to mimic the natural anatomy of the joint, and the head implant will desirably fit anatomically onto the first metatarsal, where it preferably distributes weight evenly to the underlying bone. In various embodiments, insertion of the head implant may not require the removal of excess amounts of subchondral bone, and in some embodiments the head implant can optionally include one or more contacting surfaces that desirably engage with one or more resected bone surface, such as a flattened or even undercut section 250 which engages with underlying bone to help prevent subsidence of the implant. The articulation surface 220 of the implant 200 can be configured to allow a base of a proximal phalanx guide (to be described later) to pass freely and/or glide over the top. In various embodiments, the presence of the head implant 200 will desirably prevent dorsal spur formation, and the relatively narrow thickness of the head 210 desirably allows the implant to effectively "resurface" the head of the first metatarsal while leaving much of the structural integrity of the underlying bone intact to allow for implant longevity and better function.

Figure 4:
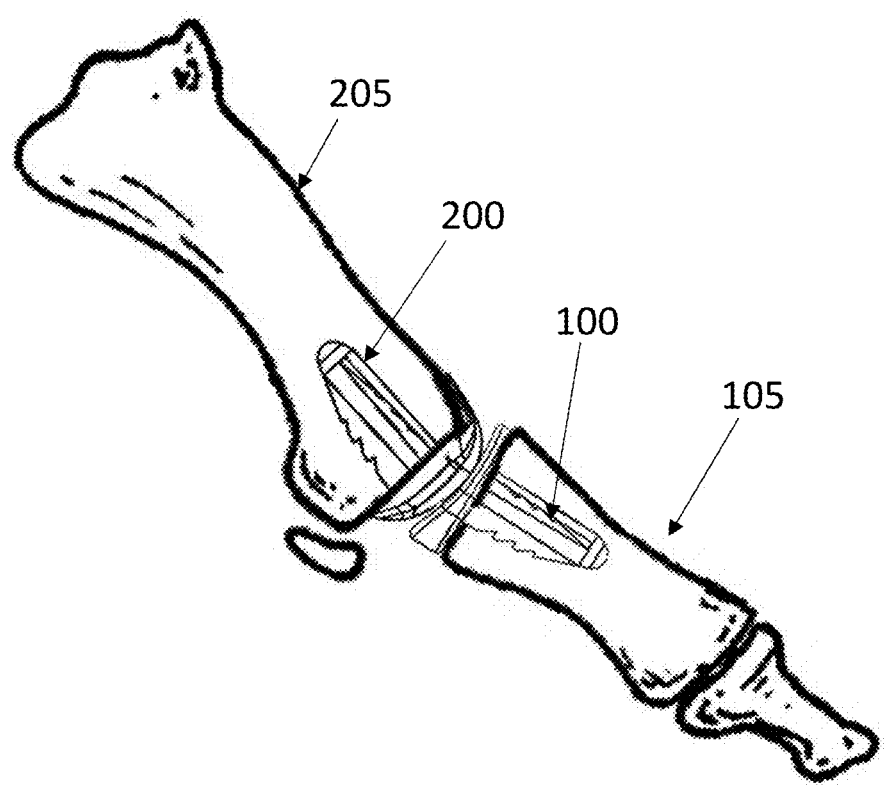
FIG. 4 depicts a side view of one exemplary embodiment of a phalanx base implant component and a metatarsal head implant component implanted into a patient's foot.
Figure 5A:
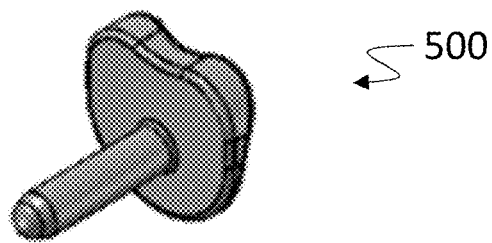
FIGS. 5A through 5D depict one exemplary embodiment of a base trial.
Figure 5B:
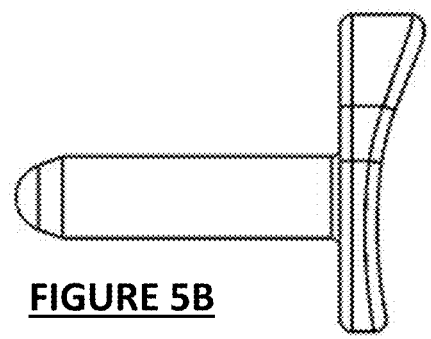
Figure 5C:
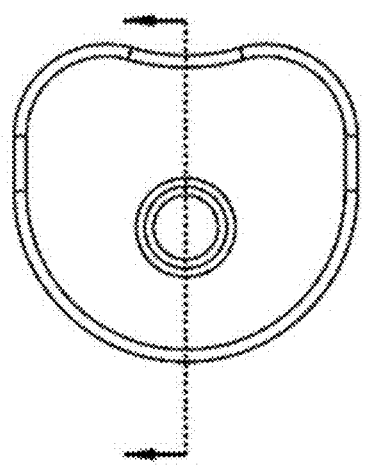
Figure 5D:
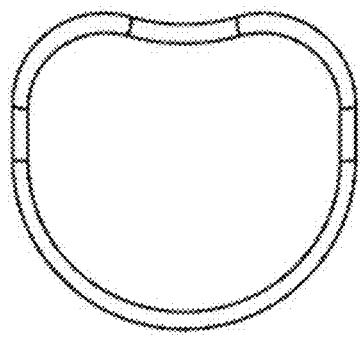
Figure 6A:
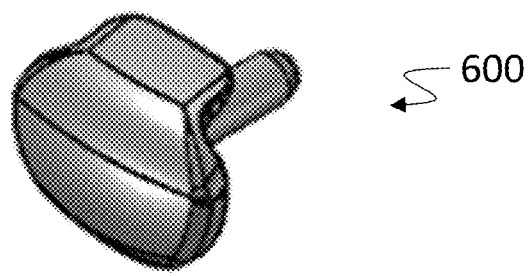
FIGS. 6A through 6E depict one exemplary embodiment of a head trial.
Figure 6B:
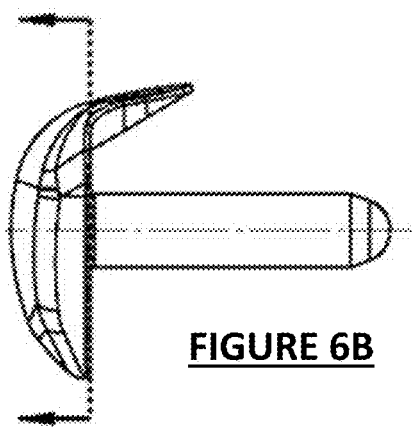
Figure 6C:
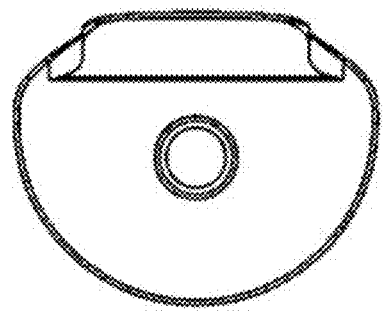
Figure 6D:
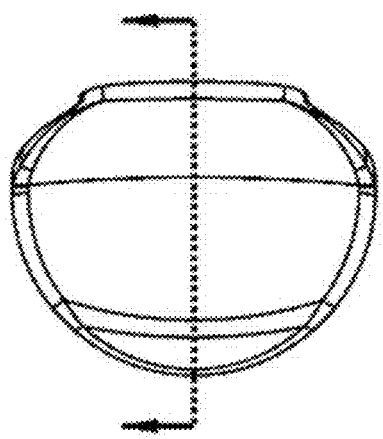
Figure 6E:
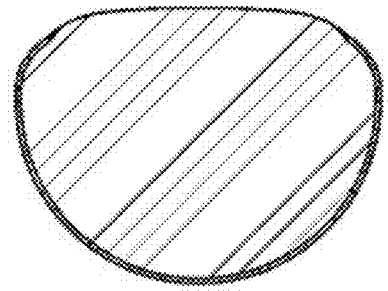

FIG. 4 depicts a side view of one exemplary embodiment of a phalanx base implant component 100 and a metatarsal head implant component 200 implanted into a proximal phalanges 105 and a first metatarsal 205 of a patient's foot, thereby forming an artificial metatarsophalangeal joint.

Figure 10:
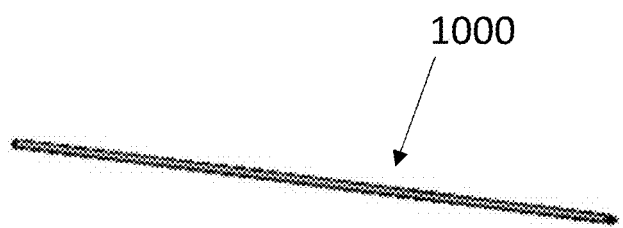
FIG. 10 depicts a perspective view of one exemplary embodiment of a guide pin or k-wire.

FIGS. 15A through 15F and 16A through 16F depict embodiments of phalanx guides 1500*a* and 1500*b*, which are designed to rest centrally on a dorsal shaft of the base of the phalanx after the base has been cleaned of articulating tissues and/or other structures. Each of the guides 1500*a* and 1500*b* includes a pair of sizing paddles (1505*a* and 1510*a* or 1505*b* and 1510*b*, respectively), which include a sizing portion that can cover the entire base (based on the surgeon's judgment), and in the disclosed embodiment the guides include at least 4 different size paddles to ensure proper fit appropriate to the patient's anatomy. During the surgical procedure, the surgeon can place each sizing paddle against the treated tissues to quickly judge the correct size of the implant and a desired proper alignment. The guide is set to allow for a k wire to be placed properly for proper fit. An opening or hole can be formed through each paddle to allow for placement of a k wire 1000 (see FIG. 10) or other securement mechanism into the bone, providing a guide to the proper position for the implant itself to rest inside the shaft of the proximal phalanx during application.

Figure 9:
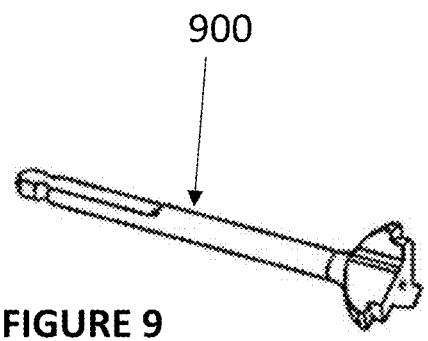
FIG. 9 depicts a perspective view of one exemplary embodiment of a reaming device.
Figure 11A:
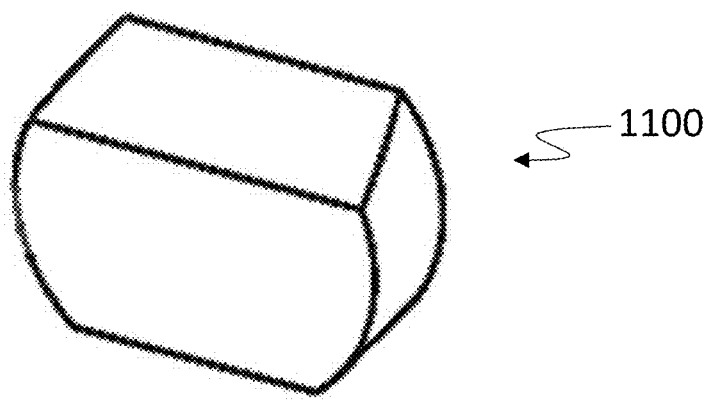
FIGS. 11A through 11C depict various views of one exemplary embodiment of a head cutting guide
Figure 11B:
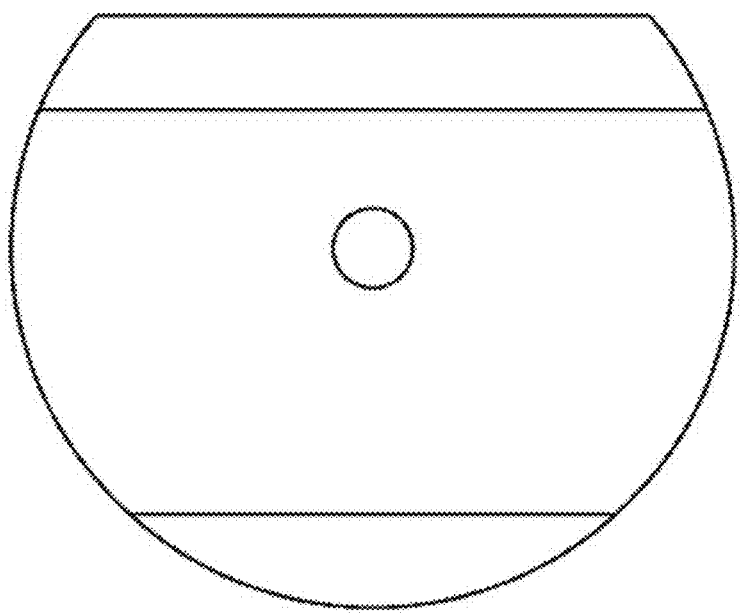
Figure 11C:
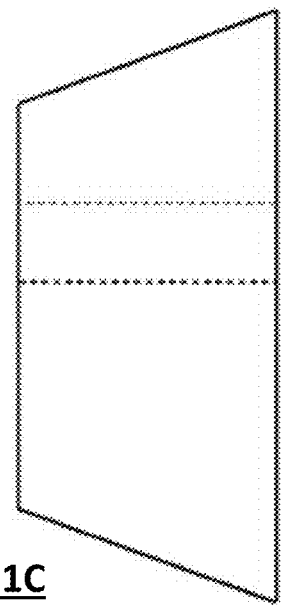
Figure 12A:
FIGS. 12A through 12F and 13A through 13F depict exemplary embodiments of metatarsal head guides.
Figure 12E:
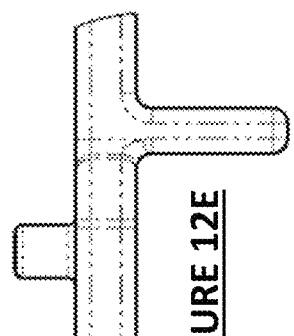
Figure 12F:
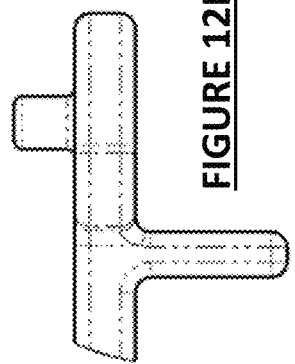
Figure 12B:
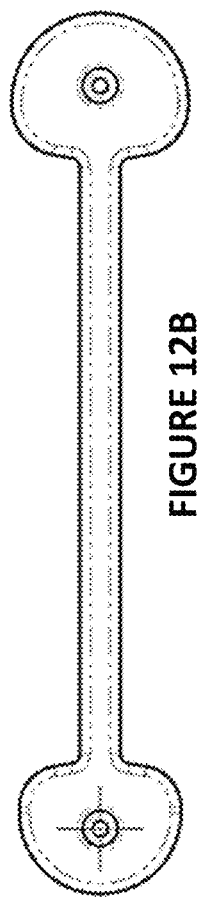
Figure 12C:
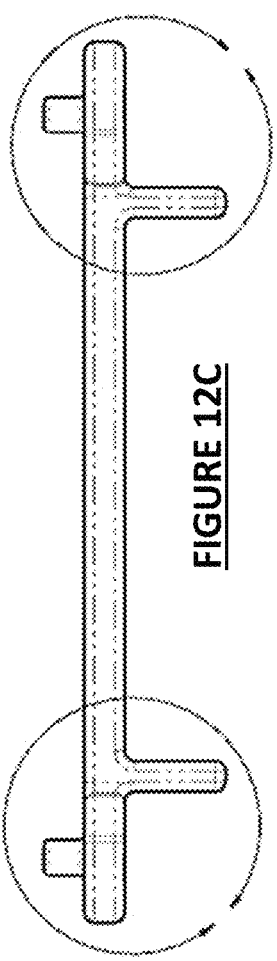
Figure 12D:
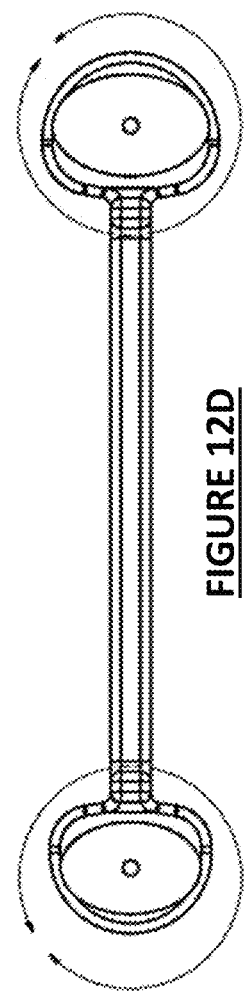
Figure 13A:
Figure 13E:
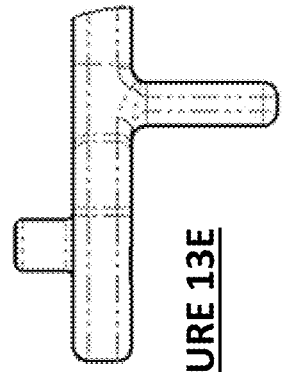
Figure 13F:
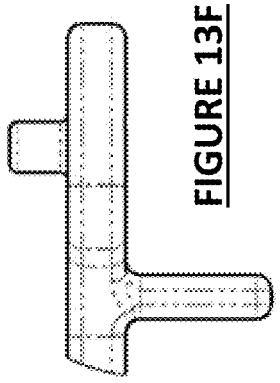
Figure 13B:
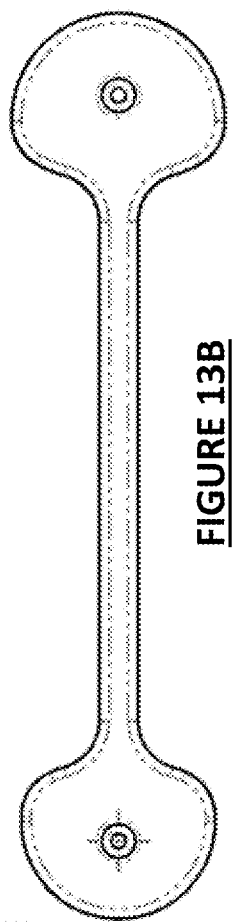
Figure 13C:
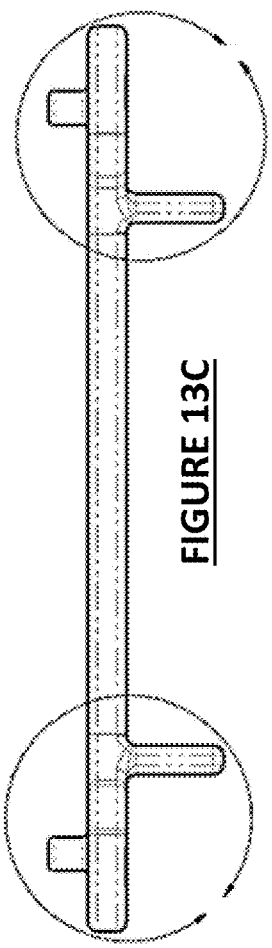
Figure 13D:
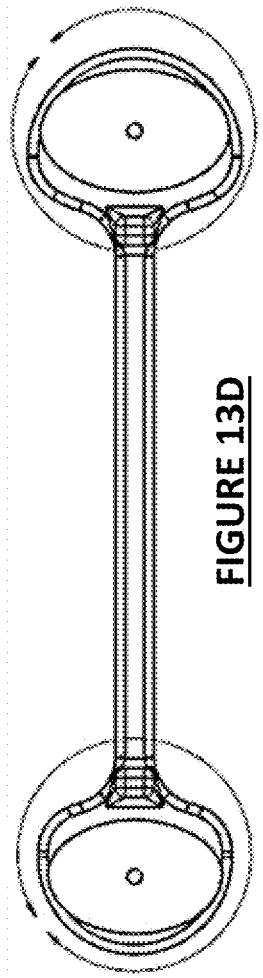

FIGS. 11A through 11C depict various views of a head cutting guide 1100, which can be designed and configured to fit into a space created by a reaming device 900 (see FIG. 9) which is used to prepare the first metatarsal. Desirably, the heads cutting guide 1100 will guide and allow a dorsal cut to be made onto the first metatarsal, thereby improving fit and performance of the final implant. In various embodiments, an appropriately sized and/or shaped head cutting guide can be provided that is specific to a given implant component size and/or shape.

Figure 14A:
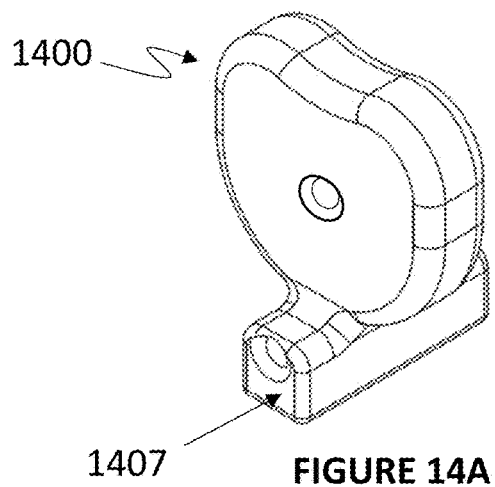
FIGS. 14A through 14C depict various views of one exemplary embodiment of a phalanx cut guide.
Figure 14D:
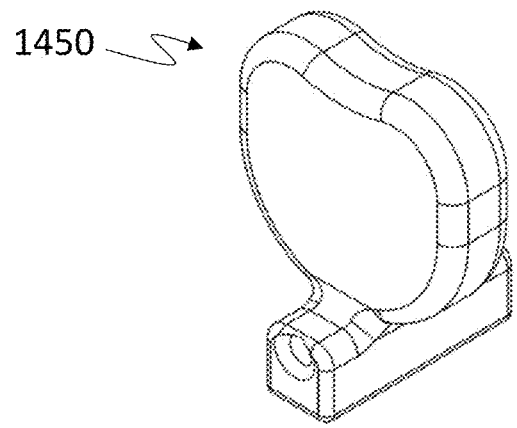
FIG. 14D depicts another exemplary embodiment of a phalanx cut guide.
Figure 14B:
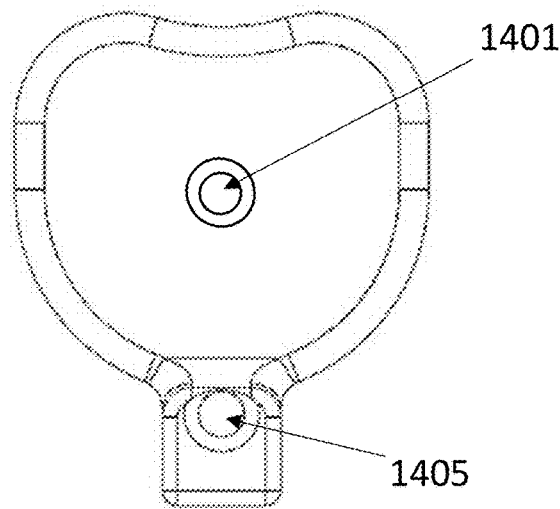
Figure 14C:
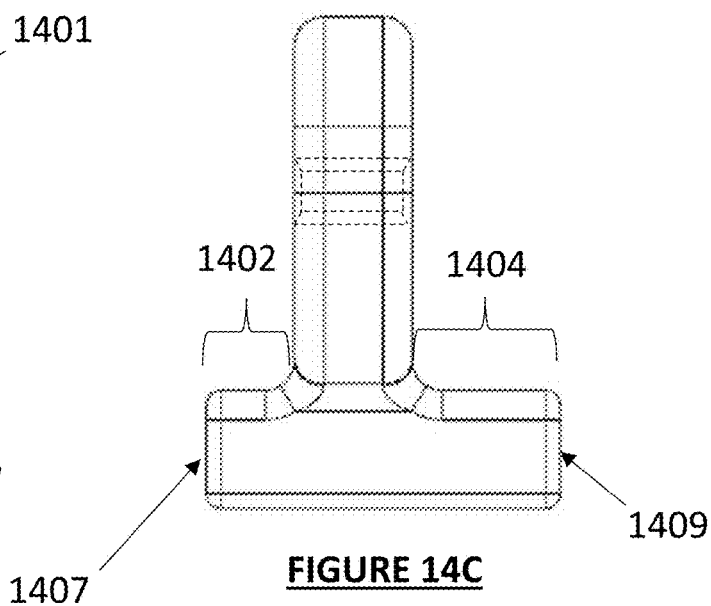
Figure 16A:
Figure 16E:
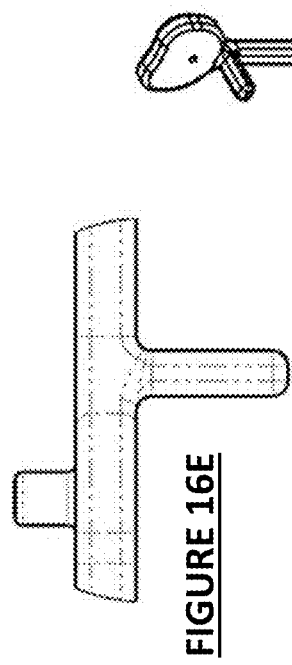
Figure 16F:
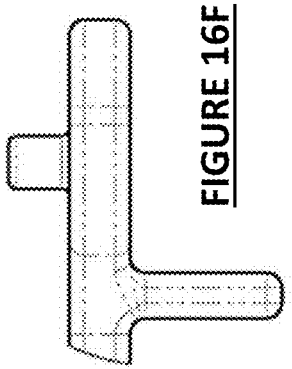
Figure 16B:
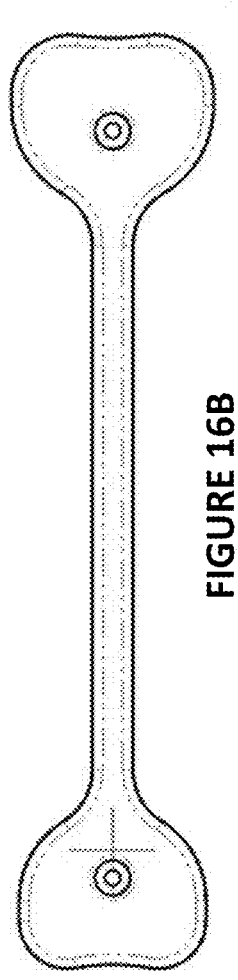
Figure 16C:
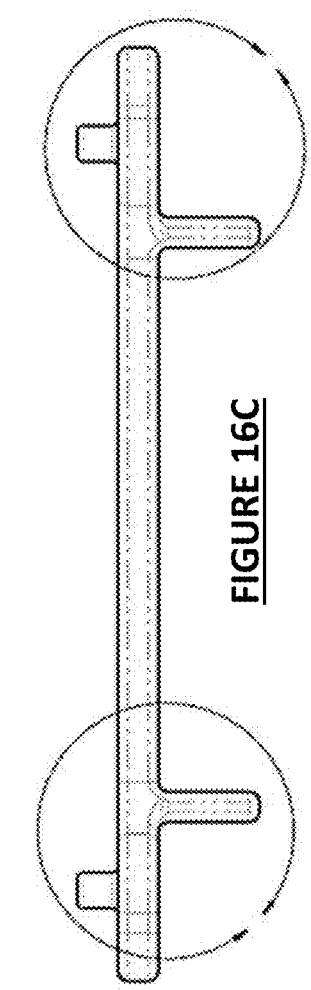
Figure 16D:
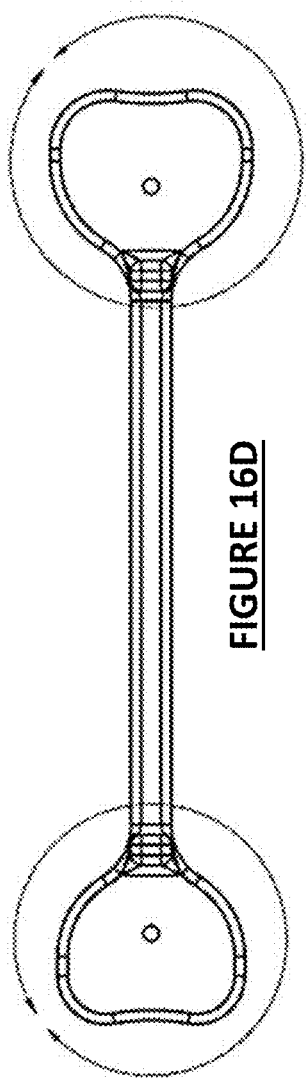

FIGS. 14A through 14C depict various views of a phalanx cut guide 1400, which in this embodiment is designed to help the surgeon plan a removal of cartilage and/or various other tissues from the base of the proximal phalanx. During the surgical procedure, once the proximal phalanx is cleaned of all spurs, the surgeon can place the phalanx cut guide 1400 on the joint surface to perform a "free hand" planar cut to remove excess cartilage angle, commonly known as an abnormal distal articular set angle or DASA. As best seen in FIG. 14C, the cut guide 1400 can include a shorter guide side 1402 and a longer guide side 1404, which in this embodiment can be lengths of 3 mm and 5 mm, respectively. In various disclosed embodiments, this cut can remove approximately 3 to 5 millimeters of bone. If desired, a guide can be provided to assist the surgeon with removing the 3 or 5 millimeters of bone, as well as help make the bone cut as perpendicular as possible to the shaft of the phalanx. Once the spurs are removed from the base, a cutting guide can be applied the base of the phalanx. Excess cartilage angle can be removed, if needed, prior to applying the guide. If desired, a dorsal cortex pin (not shown) can be put into a alignment opening 1405 to ensure that the bone cut guide 1400 is positioned generally parallel to the shaft of the phalanx, which desirably ensures that the bone cut is accomplished at the proper orientation, and in various embodiments a guide pin can be placed through a guide opening 1401 to help with sagittal plane orientation on top of the cutoff guide. A bone saw of the surgeon's choice can then be used as appropriate.

FIG. 14D depicts one alternative embodiment of a cut guide 1450 which optionally does not include a guide opening.

Figure 18A:
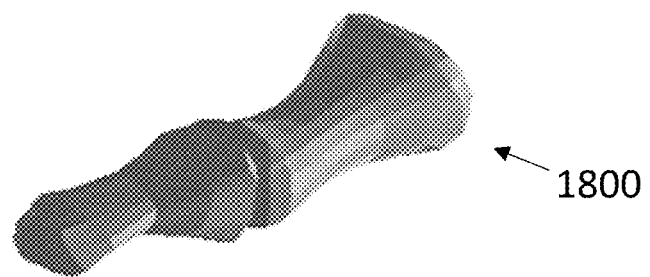
Figure 18B:
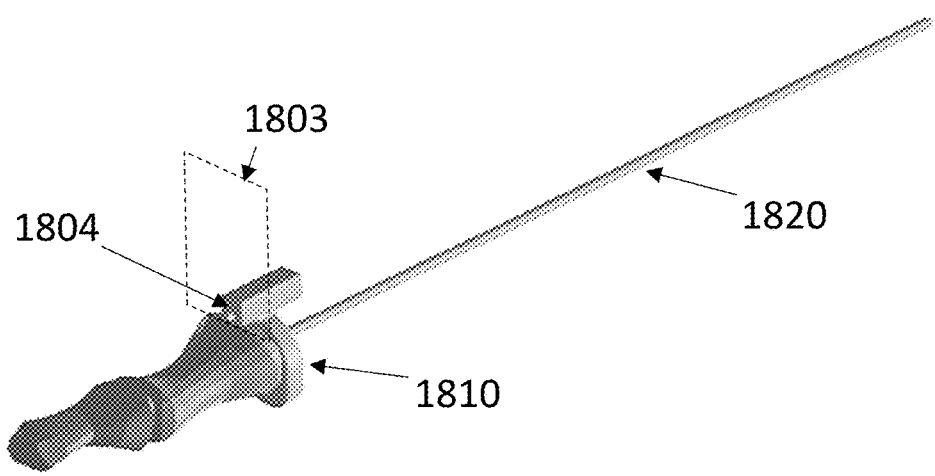

FIG. 18A depicts an exemplary stylized view of a phalanx bone 1800 of a big toe. As best seen in FIG. 18B, a phalanx cutoff guide 1800 will desirably fit onto a dorsal shaft of the proximal phalanx after any interfering spurs and/or other tissues have been removed and/or the top leveled. Depending on orientation and surgeon preference, the cutoff guide 1800 can be utilized to cut off some portion of the bone, including the described 3 to 5 mm of bone in one example (depending on the needs of the surgeon) to create a resected bone surface, desirably following a planar path 1803 which can be substantially parallel to one or more alignment surfaces 1804 of the cutoff guide (see also surface 1407 of FIGS. 14A and 14C). In various embodiments, an alignment pin (not shown) can be placed through an alignment opening to help with sagittal plane orientation on top of the cutoff guide.

Once the phalanx cutoff guide is properly positioned, a dorsal cortex pin (not shown) can be introduced, desirably so the pin is not jammed by the dorsal cortex—but rather rests on top. In various embodiments it may be desirous to change the position and/or orientation of the dorsal cortex pin and phalanx guide to obtain a correct position in the sagittal plane. The surgeon will preferably aim the dorsal cortex pin down the shaft of the phalanx to center the guide. Once satisfactory orientation is achieved, a guide pin 1820 can be placed into the appropriate guide pin hole. The positions of guide pin can be confirmed via x-ray or C-arm, if desired.

Figure 18C:
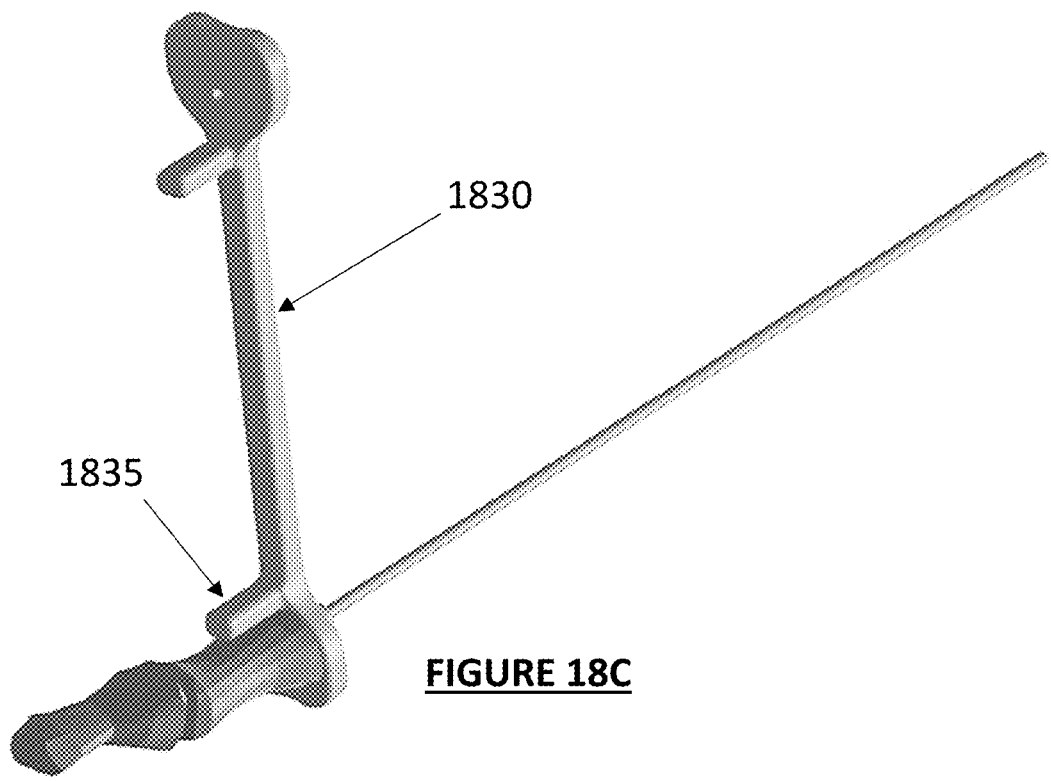

As best seen in FIG. 18C, it is then relatively easy to hold a portion of a phalanx guide 1830 over the phalanx, and a stem 1835 of the guide is desirably designed and configured to rest on top of the phalanx and line up/down relative to the shaft of the phalanx during the surgical trialing procedure. This alignment will desirably ensure that the final implant components will sit properly and have optimum function in the joint replacement. This arrangement is particularly easy to use to gauge the size and/or alignment of the phalanx and the relevant joint components therefor. In various embodiments, the guides can include a plurality of stems and related structures of differing sizes, shapes and/or angulations, which will desirably allow a single guide tool to be used with a variety of different bones to identify a corresponding implant suitable for the selected anatomy.

Figure 18D:
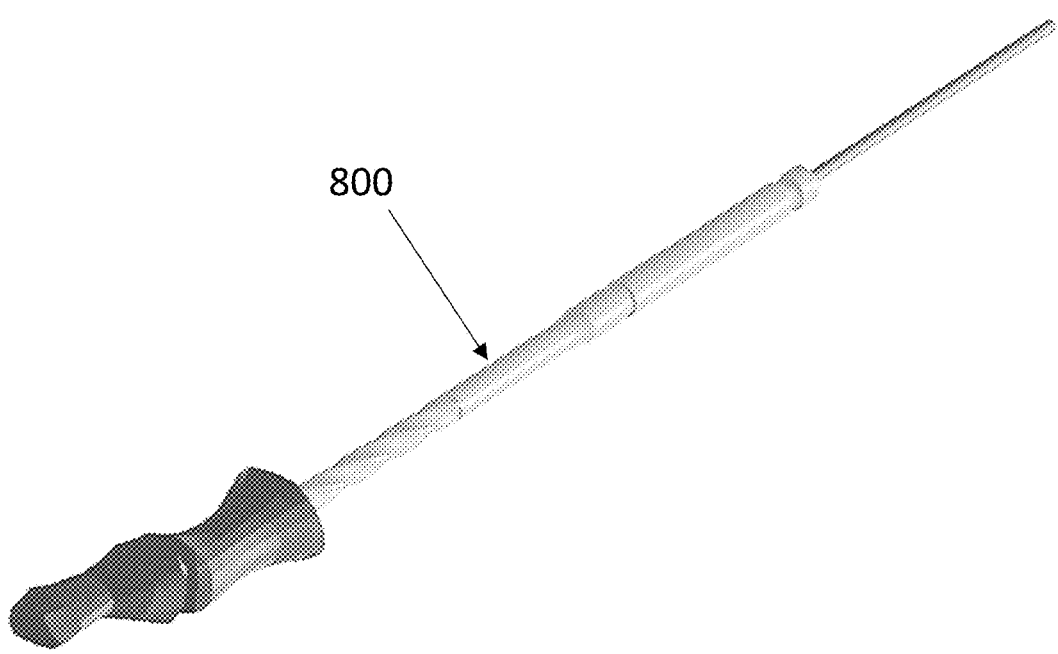

As best seen in FIG. 18C, once a surgeon has decided an appropriate guide to use for the phalanx, the guide can be removed from the phalanx and a cannulated drill bit 800 (see FIG. 18D) can be inserted over the guide pin and the guide pin can be removed. In one exemplary embodiment, the cannulated drill bit can be inserted 15 mm into the bone, which depth can be indicated by a stripe (not shown) on the drill bit. If the guide pin is still snug in the bone, a wire driver (not shown) may be used to remove it. A trial implant 1850 is then inserted into the drill hole and checked for fit (see FIGS. 18E and 18F). Once a final position is satisfactory, a triangular bone cutting device 700 (See FIGS. 7A and 18G) can be used to create bone channels to accommodate the wings of the implant. These wings on the implant will desirably stabilize the implant and prevent rotation. If only the phalanx component 1860 is being implanted, the implant may be applied at this time pending other procedures that are being done (see FIG. 18H). Bone cement can be used at the time of implant insertion at the surgeon's discretion.

FIGS. 12A through 12F and 13A through 13F depict embodiments of metatarsal head guides 1200a and 1300a which are designed and configured to desirably fit onto a head of a first metatarsal after the dorsal medial and lateral osteophytes and/or other tissues have been removed or otherwise prepared on the first metatarsal head. The metatarsal head guides 1200a and 1300a are intended to demonstrate the shape and/or alignment of the implant to the surgeon. During the surgical procedure, once the metatarsal head is cleaned of the dorsal, medial and lateral spurs, the plantar sesamoidal arms of the guide can placed between the sesamoids (i.e., the two small bones embedded within the tendon) and the metatarsal head. This activity desirably ensures the sesamoids are freed up, to allow for more and/or a desired range of anatomical motion (which is not typically provided by existing guides). If the surgeon ignores and/or forgets to free up the sesamoids, a desired level of improved motion may not be optimally obtained.

Figure 17A:
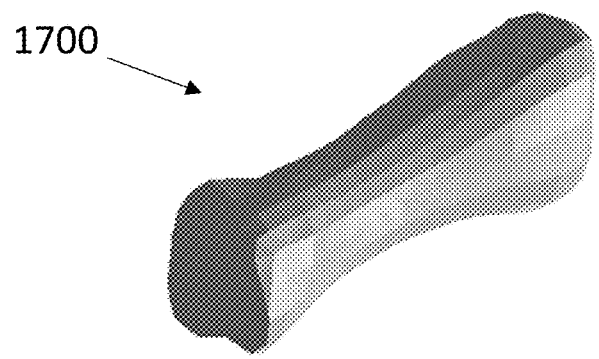
FIGS. 17A through 17H depict exemplary steps for preparing a metatarsal bone and implanting a metatarsal head implant component.
Figure 17B:
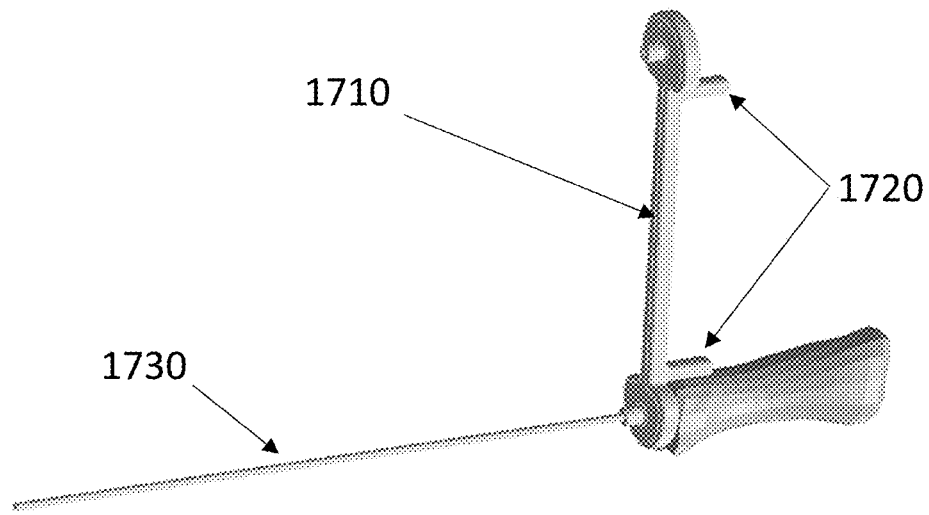

FIG. 17A depicts an exemplary stylized view of a metatarsal bone 1700. As best seen in FIG. 17B, it is relatively easy to hold a portion of a metatarsal head guide 1710 over a head of the first metatarsal, and a dorsal stem 1720 of the guide is desirably designed and configured to rest on top of a first metatarsal and line up/down relative to the shaft of the first metatarsal during the surgical trialing procedure. This alignment will desirably ensure that the final implant components will sit properly and have optimum function in the joint replacement. This arrangement is particularly easy to use to gauge the size and/or alignment of the first metatarsal and the relevant joint components therefor. In various embodiments, the guides can include a plurality of dorsal stems and related structures of differing sizes, shapes and/or angulations, which will desirably allow a single guide tool to be used with a variety of different bones to identify a corresponding implant suitable for the selected anatomy.

As best seen in FIG. 17B, once a surgeon has decided an appropriate guide to use for the metatarsal head, a pin (not shown) can be placed to help maintain the position of the guide on top of the metatarsal. This pin can be placed on top of the dorsal cortex. If there is too much motion between the dorsal cortex and the pin, a smaller size guide may be tried. Conversely, if the pin cannot rest on top of the cortex because it is blocked, then a larger size guide may be more appropriate. Once the dorsal cortex resting pin is in a proper desired position and/or placement, the pin can be used to line up the guide with the center of the metatarsal canal in the horizontal plane. Once the dorsal cortex pin is centered, a guide pin 1730 can be placed in the corresponding guide pin hole.

Figure 17C:
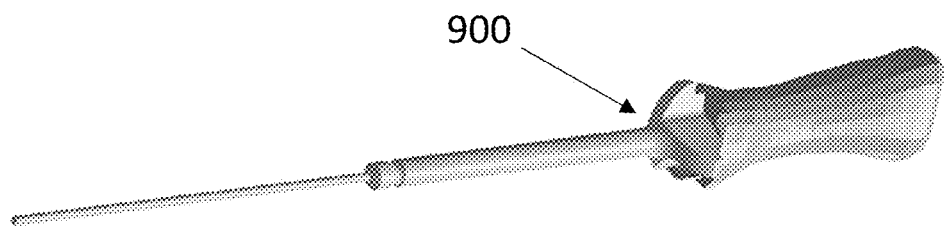

Once the dorsal cortex pin is removed from the guide, the guide 1710 can be removed from the metatarsal. A corresponding forstner bit or reamer 900 (see FIGS. 9 and 17C) can be placed over the guide pin. A hole can then be drilled using the reamer to an appropriate drill depth, which in various embodiments will desirably be indicated on the bit. In various embodiments, the present invention desirably comprises a "true" resurfacing implant which leaves a maximum amount (and/or an optimal amount) of cancellous bone on the metatarsal head. The bone that is left desirably allows for increased longevity of the joint replacement, which is in contrast to existing systems which remove a significant amount of bone.

Figure 8:
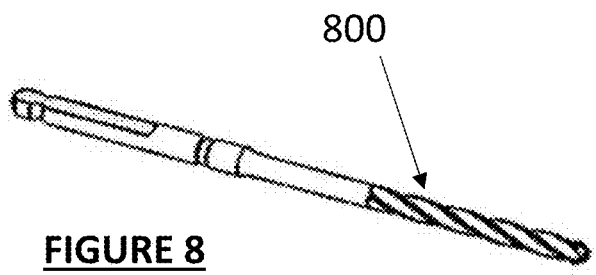
FIG. 8 depicts a perspective view of one exemplary embodiment of a cannulated drill bit.
Figure 17D:
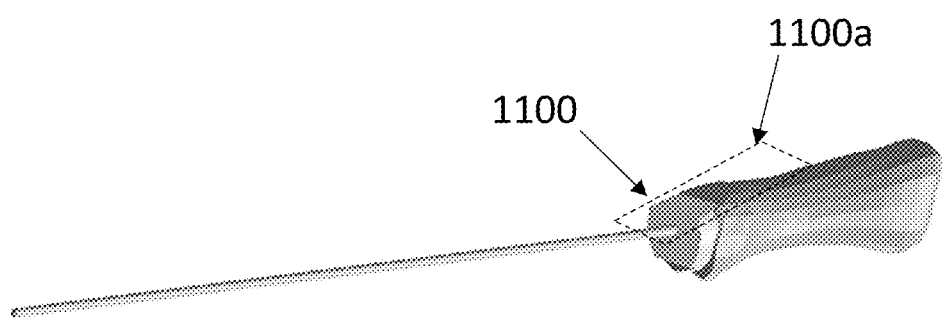
Figure 17E:
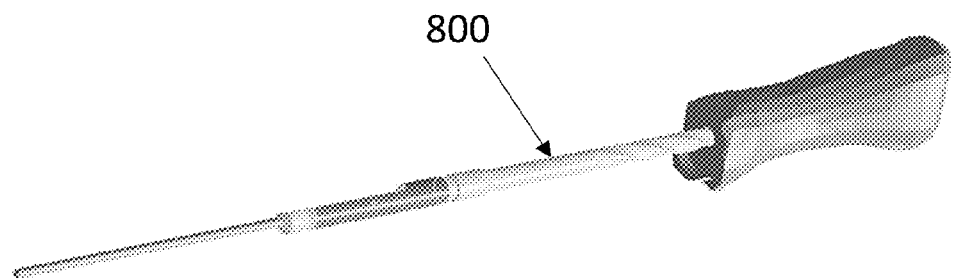

Once the bone surface is prepared, the drill bit is removed. At this time a dorsal cutting guide 1100 (see FIGS. 11A and 17D) can be applied over the guide pin, and a dorsal bone cut can be made with a bone saw of the surgeon's choice along the guide plane 1100a. This bone cut will desirably allow for the appropriate slope of the top of the implant and/or allow for improved dorsiflexion of the toe. After the dorsal bone cut is made, a cannulated drill bit 800 (See FIGS. 8 and 17E) can be inserted over the guide pin and the guide pin can be removed. In one exemplary embodiment, the cannulated drill bit can be inserted 15 mm into the bone, which depth can be indicated by a stripe (not shown) on the drill bit. If the guide pin is still snug in the bone, a wire driver (not shown) may be used to remove it.

Figure 17F:
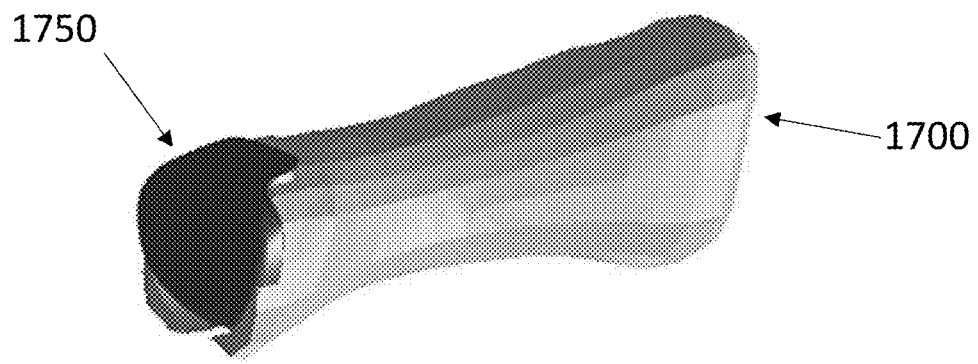

FIGS. 6A through 6E and depict one exemplary embodiment of a head trial 600 which can be utilized to show a surgeon the final resting position of the related implant components. The head trial 600 is desirably designed and configured to easily fit into a space in the metatarsal created by the various guide and cutting system components described herein. FIG. 17F depicts one exemplary embodiment of a head trial 1750 positioned on the metatarsal 1700.

Figure 17G:
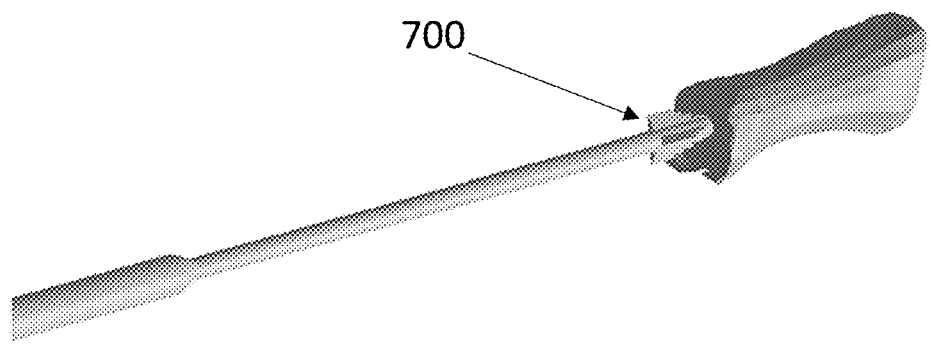

Once an appropriate head trial has been selected, the trial implant will desirably not be immediately positioned within the drill hole created in the bone. This is because a round implant will typically not properly "sit" on the medial and lateral cortices of the metatarsal, which potentially increases the risk of the implant subsiding down the shaft of the metatarsal. Instead, the surgeon will desirably use a rongeur to remove any excess bone medially and laterally from the drill hole. The surgeon may choose to remove a minimal level of bone to allow the implant trial to sit flush on the metatarsal head and may optionally choose not to remove the plantar cortex. In some embodiments, the plantar cortex is quite useful and unique and will allow the sesamoids to glide onto the implant, thereby desirably not being "jammed" by the implant. After the appropriate amount of bone is removed with the rongeur, the trial is placed into position. Once final positioning is satisfactory, a triangular bone cutting device such as a fin cutting instrument 700 (see FIGS. 7A and 17G) can be used to create bone channels to accommodate the wings of the implant, which are desirably incorporated to stabilize the implant and prevent and/or minimize implant rotation.

Figure 17H:
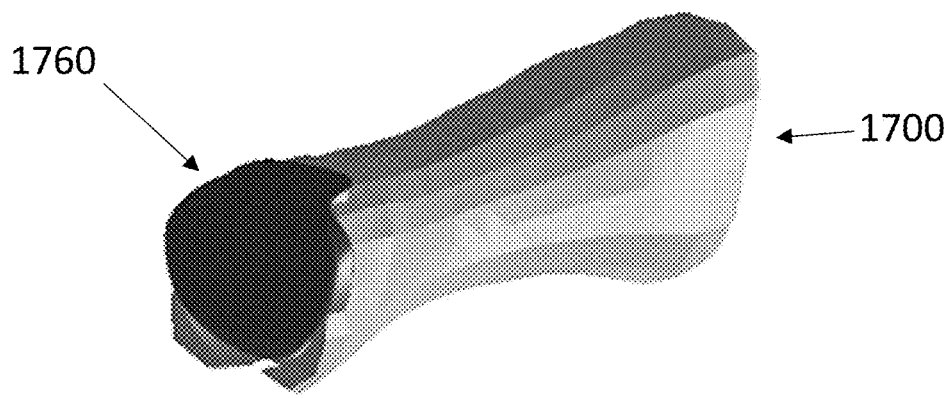

If only the metatarsal component is being implanted, the implant 1760 may be applied at this time (see FIG. 17H), pending other procedures that are being done. Bone cement can be used at the time of implant insertion at the surgeon's discretion FIGS. 5A through 5D depict one exemplary embodiment of a base trial 500 which can be utilized to show a surgeon the final resting position of the related implant components. The base trial 500 is desirably designed and configured to easily fit into a space in the phalanges created by the various guide and cutting system components described herein.

FIGS. 7A through 7D depict various views of a fin cutting instrument 700, which in this embodiment is designed to pass into a the hole in the bone created by a guide pin and/or drill bit. When properly aligned according to a relevant surgical technique guide, the fin cutting instrument can cut a plurality of slots into a corresponding shaft of a bone to allow and implant component (such as the base implant or head implant of FIGS. 2A and 3A) to fit into the corresponding shaft formed in the bone. Desirably, the fin cutting instrument matches the fins on the implant, allowing for implantation of the various finned implant components, desirably preventing rotation of the implant within the relevant anatomy.

For a joint that needs a total implant, both of the metatarsal component and phalanx component techniques can be used. In such a case, 5 mm of additional bone may need to be removed from the phalanx side to achieve a proper fit and function of the implant. If there is jamming, more bone can be removed from the phalanx side at the surgeon's discretion.

At the conclusion of the surgical procedure, an antibiotic prophylaxis such as a second-generation cephalosporine or other medication can be given intraoperatively, such as via a single-shot dose. Enoxaparin sodium may also be administered subcutaneously, such as in a dosage of 40 mg once daily, for two weeks. Early postoperative mobilization can be started on the first postoperative day, and full weight-bearing can be allowed with a postoperative shoe for six weeks. Full weight-bearing without limitations is often permitted at six weeks when patients are clinically asymptomatic and when they present no radiological signs of loosening or implant malalignment.

As disclosed herein, the combination of a thinner implant, improved surgical techniques which optimally leave more bone behind, and the employment of one or more of the dorsal, plantar, medial and lateral cortices upon which the implant can rest, desirably improves the bone support of the implant, and should result in an implant that remains fixated and stable for extended period of time and functions better over a longer period. Not only is the implant designed to facilitate minimal bone removal, but the various guides described herein allow for calculated, controlled and minimal dissection of soft tissues. Historically, over-dissection of various tissues removes vital blood supplies to a treated anatomical region and also creates significantly more scar tissue and therefore more stiffness postoperatively.

The various implant components described herein, in combination with various disclosed surgical techniques, are designed to desirably not shorten the metatarsal. Some existing implants and surgical systems carry an attendant risk of removing too much of the metatarsal head. If this happens, there is a significant risk that the implant will sit on top of the sesamoids and cause necrosis of these bones. Such undesirable outcomes have been seen in early implants with a plantar flange to articulate with the sesamoids, and such implants are no longer commonly used. If shortening of the first metatarsal is desired, such actions such be taken proximal to the implant—typically at the metatarsal diaphyseal junction or at a separate staged surgery.

Another significant improvement provided by the present system is the avoidance of a significant slanted implant surface in some embodiments, which can reduce and/or eliminate "toe cock up" or the formation of a *hallux* malleus common with slanted metatarsal implants (which typically include the slanted surfaces to aid in dorsiflexion).

In various embodiments, the disclosed implant components can desirably be plasma coated, and may include titanium on the back of the implant. Portions of the implant facing the bone will desirably include such ingrowth surfaces, but in some embodiments the shaft of the implant will not include such in-growth surfaces. If both back and shaft of the implant have bone ingrowth, then removal of the implant may be difficult where revision may be required, which can result in the creation of large deficits. Of course, in various alternative embodiments, some or all of the implant components described herein could optionally incorporate one or more bony ingrowth surfaces, which could allow natural healing and permanent fixation of these components to the bone.

As it is commonly known in the art, many joint replacement implant components (hip, knee, shoulder, etc.), will not last forever, and such may be especially true in the foot and extremities, as the bones in the foot are constantly under stress and are not particularly forgiving. For some foot and/or toe implants, so much bone may be removed in a given procedure that revisions or fusions of those joints in the future are extremely difficult and/or often require large amounts of bone graft. The present implant components and surgical procedures are intended to sacrifice very little bone upon removal, making revisions and fusions easier than with existing systems. Moreover, many of the guides and/or other tools used in conjunction with these implant components are disposable or recyclable, and can be provided in a sterile peel pack. If desired, the implant kit can be provided to a hospital in an "on demand" or "same day" delivery. Moreover, the versatility of the implant components and related surgical tools can allow the surgeon to decide perform a hemi metatarsal procedure, a hemi proximal phalanx procedure and/or a total joint replacement at the time of the surgical procedure (i.e., when the surgeon can directly visualize the joint condition) using some of all of the tools and implants provided in the surgical kit.

INCORPORATION BY REFERENCE

The entire disclosure of each of the publications, patent documents, and other references referred to herein is incorporated herein by reference in its entirety for all purposes to the same extent as if each individual source were individually denoted as being incorporated by reference.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus intended to include all changes that come within the meaning and range of equivalency of the descriptions provided herein.

Many of the aspects and advantages of the present invention may be more clearly understood and appreciated by reference to the accompanying drawings. The accompanying drawings are incorporated herein and form a part of the specification, illustrating embodiments of the present invention and together with the description, disclose the principles of the invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the disclosure herein. What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A surgical method for implanting a prosthesis into a first bone located on a first side of a metatarsophalangeal joint of a patient, comprising the steps of:
   a) accessing the metatarsophalangeal joint through a surgical incision;
   b) placing a surgical guide tool against an articulating surface of the first bone, the surgical guide tool having a plurality of different guide trialing surfaces, the surgical guide tool including at least one opening formed therethrough to accommodate a guide pin;
   c) inserting the guide pin through the at least one opening and into an intramedullary channel within the first bone to create a first passage,
   d) removing at least a portion of the articulating surface from the first bone to create a resected surface;
   e) drilling the intramedullary channel to increase the size of the first passage;
   f) inserting a trial prosthesis into the drilled first passage and check for fit and final resting position of a permanent prosthesis;
   g) creating a plurality of elongated grooves within an outer wall of the first passage; and
   h) placing a base portion of the permanent prosthesis within the first passage, the base portion having a plurality of anchoring wings complementary to size and shape of the plurality of elongated grooves, the anchoring wings being positioned within the plurality of elongated grooves, the prosthesis including a contacting surface which abuts against the resected surface, wherein each of the guide trialing surfaces comprises a substantially planar sizing paddle with a size, shape, and angulation configured to identify the correct size and shape of the base portion of the prosthesis and a desired proper alignment of the prosthesis, wherein said at least one opening is formed through the sizing paddle, and wherein each of the guide trialing surfaces further comprises a guide stem extending perpendicular from the sizing paddle and sized and configured to rest on top of the first bone and line up/down relative to the shaft of the first bone, wherein said guide stem comprises an alignment opening formed therethrough to accommodate a dorsal cortex pin, wherein the first bone is one of a metatarsal bone or a phalanx bone.

2. The surgical method of claim 1, wherein at least some portion of the contacting surface includes a bone in-growth surface.

3. The surgical method of claim 2, wherein the base portion does not incorporate a bone in-growth surface.

* * * * *